US008106037B2

(12) United States Patent
Rubin et al.

(10) Patent No.: US 8,106,037 B2
(45) Date of Patent: Jan. 31, 2012

(54) IDENTIFICATION AND TREATMENT OF ESTROGEN RESPONSIVE PROSTATE TUMORS

(75) Inventors: Mark Rubin, New York, NY (US); Kirsten Mertz, Liestal (CH); Sunita Setlur, Ashland, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 559 days.

(21) Appl. No.: 12/219,528

(22) Filed: Jul. 23, 2008

(65) Prior Publication Data
US 2009/0036415 A1 Feb. 5, 2009

Related U.S. Application Data

(60) Provisional application No. 60/935,299, filed on Aug. 3, 2007.

(51) Int. Cl.
A61K 31/56 (2006.01)
A61K 38/00 (2006.01)
(52) U.S. Cl. .......................... 514/182; 514/1.1; 514/177
(58) Field of Classification Search .................. None
See application file for complete search history.

(56) References Cited

U.S. PATENT DOCUMENTS

| | | | |
|---|---|---|---|
| 5,856,125 | A | 1/1999 | Mavrothalassitis |
| 6,043,033 | A | 3/2000 | Bandman et al. |
| 6,166,194 | A | 12/2000 | Wong et al. |
| 6,350,448 | B1 | 2/2002 | Bandman et al. |
| 6,395,278 | B1 | 5/2002 | Xu et al. |
| 6,444,419 | B1 | 9/2002 | Wong et al. |
| 6,872,811 | B1 | 3/2005 | MacBeth et al. |
| 6,902,892 | B1 | 6/2005 | Salceda et al. |
| 7,037,667 | B1 | 5/2006 | Afar et al. |
| 7,125,969 | B1 | 10/2006 | Benz et al. |
| 7,718,369 | B2 | 5/2010 | Tomlins et al. |
| 7,737,255 | B1 | 6/2010 | Salceda et al. |
| 2002/0119531 | A1 | 8/2002 | Bandman et al. |
| 2002/0182586 | A1 | 12/2002 | Morris et al. |
| 2003/0103981 | A1 | 6/2003 | Spancake |
| 2003/0108963 | A1 | 6/2003 | Schlegel et al. |
| 2003/0170625 | A1 | 9/2003 | Rosenthal et al. |
| 2004/0009481 | A1 | 1/2004 | Schlegel et al. |
| 2004/0259086 | A1 | 12/2004 | Schlegel et al. |
| 2005/0009086 | A1 | 1/2005 | Salceda et al. |
| 2005/0158241 | A1 | 7/2005 | Salceda et al. |
| 2005/0158242 | A1 | 7/2005 | Salceda et al. |
| 2005/0158608 | A1 | 7/2005 | Shu et al. |
| 2006/0228710 | A1 | 10/2006 | Morris et al. |
| 2007/0212702 | A1 | 9/2007 | Tomlins |
| 2007/0275915 | A1 | 11/2007 | Hallenbeck et al. |
| 2009/0047269 | A1 | 2/2009 | Chinnaiyan et al. |
| 2009/0075284 | A1 | 3/2009 | Chinnaiyan et al. |
| 2009/0170075 | A1 | 7/2009 | Petrovics et al. |
| 2009/0208937 | A1 | 8/2009 | Chinnaiyan et al. |
| 2009/0239221 | A1 | 9/2009 | Chinnaiyan et al. |
| 2010/0284910 | A1 | 11/2010 | Salceda et al. |

FOREIGN PATENT DOCUMENTS

| | | |
|---|---|---|
| WO | WO 99/62942 A2 | 12/1999 |
| WO | WO 99/65929 A1 | 12/1999 |
| WO | WO 00/00605 A1 | 1/2000 |
| WO | WO 00/04149 A2 | 1/2000 |
| WO | WO 00/23111 A1 | 4/2000 |
| WO | WO 0018961 A2 | 4/2000 |
| WO | WO 00/65067 A2 | 11/2000 |
| WO | WO 0070092 A1 | 11/2000 |
| WO | WO 01/53836 A2 | 7/2001 |
| WO | WO 01/60860 A2 | 8/2001 |
| WO | WO 01/88124 A2 | 11/2001 |
| WO | WO 03/009814 A2 | 2/2003 |
| WO | WO 03/053223 A2 | 7/2003 |
| WO | WO 2004/023973 A2 | 3/2004 |
| WO | WO 2004/097358 A2 | 11/2004 |
| WO | WO 2004/113571 A2 | 12/2004 |
| WO | WO 2007/033187 | 3/2007 |
| WO | WO 2009/009432 A2 | 1/2009 |

OTHER PUBLICATIONS

Mertz et al (Neplasia 9:200-206, Mar. 2007.*
Hermans (Cancer Res. 66:10658-63, Nov. 2006.*
Clinical trials for prostate cancer by Fulvestrant (NCT00217464), Oct. 25, 2005.*
Medscape online publication (2001).*
Online pub fulvestrant doss (Feb. 2, 2000).*
Tomlins et al, Science, 310:644-48, 2005.*
Attard, et al., "Duplication of the fusion of TMPRSS2 to ERG sequences identifies fatal human prostate cancer," Oncogene 27:253-263 (2008); ( published online Jul. 16, 2007).
Barry, et al., "TMPRSS2-ERG Fusion Heterogeneity in Multifocal Prostate Cancer: Clinical and Biologic Implications," Urology 70(4):630-633 (2007).
Carroll, et al., "Genome-wide analysis of estrogen receptor binding sites," Nat. Genet. 38(11):1289-1297 (Nov. 2006).
Demichelis, et al., "TMPRSS2:ERG gene fusion associated with lethal prostate cancer in a watchful waiting cohort," Oncogene 26:4596-4599 (2007); ( published online Jan. 22, 2007).
Demichelis, et al., "TMPRSS2-ETS fusion prostate cancer: biological and clinical implications," J. Clin. Pathol. 60:1185-1186 (2007).
Fixemer, et al., "Differential Expression of the Estrogen Receptor Beta (ERβ) in Human Prostate Tissue, Premalignant Changes, and in Primary, Metastatic, and Recurrent Prostatic Adenocarcinoma," Prostate 54:79-87 (2003).
Hartel, et al., "Characterisation of steroid receptor expression in the human prostate carcinoma cell line 22RV1 and quantification of androgen effects on mRNA regulation of prostate-specific genes," J. Steroid Biochem. Mol. Biol. 92:187-197 (2004).

(Continued)

Primary Examiner — Misook Yu
Assistant Examiner — Lei Yao
(74) Attorney, Agent, or Firm — Law Office of: Michael A. Sanzo, LLC

(57) ABSTRACT

The present invention is directed to specific chromosomal rearrangements that are associated with prostate tumors that respond to compounds acting at estrogen receptors. Patients having the TMPRSS2-ERG fusion, may be treated with agonists of the estrogen beta receptor or antagonists of the estrogen alpha receptor.

20 Claims, No Drawings

OTHER PUBLICATIONS

Lamb, et al., "The Connectivity Map: Using Gene-Expression Signatures to Connect Small Molecules, Genes, and Disease," 313:1929-1935 (Sep. 2006).
Lin, et al., "Prostate-localized and Androgen-regulated Expression of the Membrane-bound Serine Protease TMPRSS2[1]," *Cancer Res.* 59:4180-4184 (Sep. 1999).
Mertz, et al., "Molecular Characterization of *TMPRSS2-ERG* Gene Fusion in the NCI-H660 Prostate Cancer Cell Line: A New Perspective for an Old Model[1]," *Neoplasia* 9(3):200-206 (Mar. 2007).
Pasquali, et al., "Loss of Estrogen Receptor β Expression in Malignant Human Prostate Cells in Primary Cultures and in Prostate Cancer Tissues," *J. Clin. Endocrinol. Metab.* 86(5):2051-2055 (2001).
Perner, et al., "*TMPRSS2-ERG* Fusion-Associated Deletions Provide Insight into the Heterogeneity of Prostate Cancer," *Cancer Res.* 66(17):8337-8341 (Sep. 2006).
Rajput, et al., "Frequency of the TMPRSS2:ERG gene fusion is increased in moderate to poorly differentiated prostate cancers," *J. Clin. Pathol.* 60:1238-1243 (2007); (published online Jan. 26, 2007).
Rhodes, et al., "Molecular Concepts Analysis Links Tumors, Pathways, Mechanisms, and Drugs," *Neoplasia* 9(5):443-454 (May 2007).
Schröder, et al., "Re: Recurrent Fusion of TMPRSS2 and ETS Transcription Factor Genes in Prostate Cancer," *European Urology* 51:1443-1444 (2007).
Schröder, et al., "Re: Duplication of the Fusion of TMPRSS2 to ERG Sequences Identifies Fatal Human Prostate Cancer," *European Urology* 53:208-211 (2008).
Slentz-Kesler, et al., "Identification of the Human Mnk2 Gene (MKNK2) through Protein Interaction with Estrogen Receptor β," *Genomics* 69:63-71 (2000).
Tomlins, et at,"*TMPRSS2:ETV4* Gene Fusion Define a Third Molecular Subtype of Prostate Cancer," *Cancer Res.* 66(7):3396-3400 (Apr. 2006).
Tomlins, et al., "Recurrent Fusion of *TMPRSS2* and ETS Transcription Factor Genes in Prostate Cancer," *Science* 310:644-648 (Oct. 2005).
Tomlins, et al., "Integrative molecular concept modeling of prostrate cancer progression," *Nat Genet.*. 39(1):41-51 (Jan. 2007).
International Search Report for PCT/US2008/008904 filed Jul. 23, 2008.
Written Opinion of the International Searching Authority for PCT/US2008/008904 filed Jul. 23, 2008.
International Preliminary Report on Patentability for PCT/US2008/008904 filed Jul. 23, 2008.
Abdulkadir, et al., "Conditional Loss of *Nkx3.1* in Adult Mice Induces Prostatic Intraepithelial Neoplasia," *Mol. Cell. Biol.* 22(5):1495-1503 (Mar. 2002).
Afar, et al., "Catalytic Cleavage of the Androgen-regulated TMPRSS2 Protease Results in Its Secretion by Prostate and Prostate Cancer Epithelia," *Cancer Res.* 61:1686-1692 (Feb. 2001).
Ahlers, et al., "ETS-TMPRSS2 Fusion Gene Products in Prostate Cancer," *Cancer Biology & Therapy* 5(3):254-255 (Mar. 2006).
Antoniou, et al., "Transgenes encompassing dual-promoter CpG islands from human TBP and HNRPA2B1 loci are resistant to heterochromatin-mediated silencing," *Genomics* 82:269-279 (2003).
Beheshti, et al., "Evidence of Chromosomal Instability in Prostate Cancer Determined by Spectral Karyotyping (SKY) and Interphase FISH Analysis," *Neoplasia* 3(1):62-69 (2001).
Beheshti, et al., "Identification of a High Frequency of Chromosomal Rearrangements in the Centromeric Regions of Prostate Cancer Cell Lines by Sequential Giemsa Banding and Spectral Karyotyping," *Molecular Diagnosis* 5(1):23-32 (2000).
Bittner, et al., "Molecular classification of cutaneous malignant melanoma by gene expression profiling," *Nature* 406:536-540 (Aug. 2000).
Bonkhoff, et al., "Estrogen Receptor Expression in Prostate Cancer and Premalignant Prostatic Lesions," *Am. J. Pathol.* 155(2):641-647 (Aug. 1999).
Bonkhoff, et al., "Progesterone Receptor Expression in Human Prostate Cancer: Correlation With Tumor Progression," *The Prostate* 48:285-291 (2001).

Cai, et al., "ETV1 Is a Novel Androgen Receptor-Regulated Gene that Mediates Prostate Cancer Cell Invasion," *Molecular Endocrinology* 21(8):1835-1846 (2007).
Cerveira, et al., "TMPRSS2-ERG Gene Fusion Causing ERG Overexpression Precedes Chromosome Copy Number Changes in Prostate Carcinomas and Paired HGPIN Lesions," *Neoplasia* 8(10):826-832 (Oct. 2006).
Chen, et al., "Variation in Gene Expression Patterns in Human Gastric Cancers," *Mol. Biol. Cell* 14:3208-3215 (Aug. 2005).
Cheng, et al., "Expression of estrogen receptor β in prostate carcinoma cells inhibits invasion and proliferation and triggers apoptosis," *FEBS Letters* 566:169-172 (2004).
Cheok, et al., "Treatment-specific changes in gene expression discriminate in vivo drug response in human leukemia cells," *Nature Genetics* 34:85-90 (May 2003).
Deininger, et al., "The development of imatinib as a therapeutic agent for chronic myeloid leukemia," *Blood* 105(7):2640-2653 (Apr. 2005).
De Klein, et al., "A cellular onogene is translocated to the Philadelphia chromosome in chronic myelocytic leukaemia," *Nature* 300:765-767 (Dec. 1982).
Dhanasekaran, et al., "Molecular profiling of human prostate tissues: insights into gene expression patterns of prostate development during puberty," *FASEB Journal* 19:243-245 (Feb. 2005).
Di Cristofano, et al., "Pten and $p27^{KIP1}$ cooperate in prostate cancer tumor suppression in the mouse," *Nature Genetics* 27:222-224 (Feb. 2001).
Eisen, et al., "Cluster analysis and display of genome-wide expression patterns," *Proc. Natl. Acad. Sci. USA* 95(25):14863-14868 (Dec. 1998).
Eisenberg, et al., "Human housekeeping genes are compact," *TRENDS in Genetics* 19(7):362-365 (Jul. 2003).
Ferrando, et al., "Gene expression signatures define novel oncogenic pathways in T cell acute lymphoblastic leukemia," *Cancer Cell* 1:75-87 (Feb. 2002).
Fingleton, et al., "Matrix metalloproteinases: roles in cancer and metastasis," *Frontiers in Bioscience* 11:479-491 (Jan. 2006).
Fonseca, et al., "Genetics and Cytogenetics of Multiple Myeloma: A Workshop Report," *Cancer Res.* 64:1546-1558 (Feb. 2004).
Garraway, et al., "Integrative genomic analyses identify *MITF* as a lineage survival oncogene amplified in malignant melanoma," *Nature* 436:117-122 (Jul. 2005).
Gibas, et al., "A High-Resolution Study of Chromosome Changes in a Human Prostatic Carcinoma Cell Line (LNCaP)," *Cancer Genetics & Cytogenetics* 11:399-404 (1984).
Golub, et al., "Molecular Classification of Cancer: Class Discovery and Class Prediction by Gene Expression Monitoring," *Science* 286:531-537 (Oct. 1999).
Guasch, et al., "Endogenous retroviral sequence is fused to FGFR1 kinase in the 8p12 stem-cell myeloproliferative disorder with t(8;19)(p12;q13.3)," *Blood* 101(1):286-288 (Jan. 2003).
Han, et al., "A Fluorescence in situ Hybridization Screen for E26 Transformation—Specific Aberrations: Identification of DDX5-ETV4 Fusion Protein in Prostate Cancer," *Cancer Res.* 68:7629-7637 (Sep. 2008).
Hattori, et al., "The DNA sequence of human chromosome 21," *Nature* 405:311-319 (May 2000).
Helgeson, et al., "Characterization of TMPRSS2:ETV5 and SLC45A3:ETV5 Gene Fusions in Prostate Cancer," *Cancer Res.* 68(1):73-80 (Jan. 2008).
Hendriksen, et al., "Evolution of the Androgen Receptor Pathway during Progression of Prostate Cancer," *Cancer Res.* 66(10):5012-5020 (May 2006).
Hermans, et al., "*TMPRSS2:ERG* Fusion by Translocation or Interstitial Deletion Is Highly Relevant in Androgen-Dependent Prostate Cancer, But Is Bypassed in Late-Stage Androgen Receptor-Negative Prostate Cancer," *Cancer Res.* 66(22):10658-10663 (Nov. 2006).
Hermans, et al., "Truncated ETV1, Fused to Novel Tissue-Specific Genes, and Full-Length ETV1 in Prostate Cancer," *Cancer Res.* 68(18):7541-7549 (Sep. 2008).
Heresi, et al., "Expression of the chemokine receptor CCR7 in prostate cancer presenting with generalized lymphadenopathy: Report of a case, review of literature, and analysis of chemokine receptor expression," *Urologic Oncology* 23:261-267 (2005).
Huang, et al., "Gene expression predictors of breast cancer," *The Lancet* 361:1590-1596 (May 2003).
Iljin, et al., "TMPRSS2 Fusions with Oncogenic ETS Factors in Prostate Cancer Involve Unbalanced Genomic Rearrangements and Are Associated with HDAC1 and Epigenetic Reprogramming," *Cancer Res.* 66(21):10242-10246 (Nov. 2006).
Imamov, et al., "Estrogen Receptor beta in Health and Disease," *Biol. Reprod.* 73:866-871 (2005).
Jacquinet, et al., "Cloning and characterization of the cDNA and gene for human epitheliasin," *Eur. J. Biochem.* 268:2687-2699 (2001).
Jain, et al., "Expression Profiles Provide Insights into Early Malignant Potential and Skeletal Abnormalities in Multiple Endocrine Neoplasia Type 2B Syndrome Tumors," *Cancer Res.* 64:3907-3913 (2004).
Jemal, et al., "Cancer Statistics, 2007," *CA Cancer J. Clin.* 57:43-66 (2007).
Kalos, et al., "Prostein Expression Is Highly Restricted to Normal and Malignant Prostate Tissues," *The Prostate* 60:246-256 (2004).
Keats, et al., "Overexpression of transcripts originating from the MMSET locus characterizes all t(4;14)(p16;q32)-positive multiple myeloma patients," *Blood* 105(10):4060-4069 (May 2005).
Kim, et al., "Cooperativity of *Nkx3.1* and *Pten* loss of function in a mouse model of prostate carcinogenesis," *PNAS* 99(5):2884-2889 (Mar. 2002).
Kumar-Sinha, et al., "Evidence of recurrent gene fusions in common epithelial tumors," *Trends Mol. Medicine* 12(11):529-536 (2006).
Kumar-Sinha, et al., "Recurrent gene fusions in prostate cancer," *Nature Reviews*, Cancer 8:497-511 (Jul. 2008).
Lapointe, et al., "Gene expression profiling identifies clinically relevant subtypes of prostate cancer," *PNAS* 101(3):811-816 (Jan. 2004).
Latulippe, et al., "Comprehensive Gene Expression Analysis of Prostate Cancer Reveals Distinct Transcriptional Programs Associated with Metastatic Disease," *Cancer Res.* 62:4499-4506 (Aug. 2002).
Lau, et al., "Expression of Estrogen Receptor (ER)-α and ER-β in Normal and Malignant Prostatic Epithelial Cells: Regulation by Methylation and Involvement in Growth Regulation," *Cancer Res.* 60:3175-3182 (Jun. 2000).
Laxman, et al., "Noninvasive Detection of *TMPRSS2:ERG* Fusion Transcripts in the Urine of Men with Prostate Cancer," *Neoplasia* 8(I0):885-888 (Oct. 2006).
Mehra, et al., "Comprehensive assessment of *TMPRSS2* and *ETS* family gene aberrations in clinically localized prostate cancer," *Modern Pathology* 20:538-544 (2007).
Mimeault, et al., "Novel combination therapy against metastatic and androgen-independent prostate cancer by using gefitinib, tamoxifen and etoposide," *Int. J. Cancer* 120:160-169 (2006).
Mirosevich, et al., "Expression and Role of Foxa Proteins in Prostate Cancer," *The Prostate* 66:1013-1028 (2006).
Mirosevich, et al., "Expression of Foxa Transcription Factors in the Developing and Adult Murine Prostate," *The Prostate* 62:339-352 (2005).
Mitelman, "Recurrent chromosome aberrations in cancer," *Mutation Research* 462:247-253 (2000).
Morris, et al., "The discovery and application of gene fusions in prostate cancer," *BJU International* 102:276-282 (2008).
Mosquera, et al., "Morphological features of *TMPRSS2-ERG* gene fusion prostate cancer," *J. Pathol.* 212:91-101 (2007).
Murillo, et al., "Prostate Cancer Cells Use Genetic and Epigenetic Mechanisms for Progression to Androgen Independence," *Genes, Chromosomes & Cancer* 45:702-716 (2006).
Nam, et al., "Expression of TMPRSS2 ERG Gene Fusion in Prostate Cancer Cells is an Important Prognostic Factor for Cancer Progression," *Cancer Biology & Therapy* 6(1):40-45 (2007).
Oettgen, et al., "PDEF, a Novel Prostate Epithelium-specific Ets Transcription Factor, Interacts with the Androgen Receptor and Activates Prostate-specific Antigen Gene Expression," J. Biol. Chem. 275(2):1216-1225 (2000).
Ono, et al., "Stimulation of Expression of the Human Endogenous Retrovirus Genome by Female Steroid Hormones in Human Breast Cancer Cell Line T47D," *J. Virol.* 61(6):2059-2062 (Jun. 1987).

Owczarek, et al., "Detailed mapping of the ERG-ETS2 interval of human chromosome 21 and comparison with the region of conserved synteny on mouse chromosome 16," *Gene* 324:65-77 (2004).
Pang, et al., "Cytogenetic and Expression Profiles Associated With Transformation to Androgen-Resistant Prostate Cancer," *The Prostate* 66:157-172 (2006).
Paoloni-Giacobino, et al., "Cloning of the TMPRSS2 Gene, Which Encodes a Novel Serine Protease with Transmembrane, LDLRA, and SRCR Domains and Maps to 21q22.3," *Genomics* 44(3):309-320 (1997).
Paris, et al., "Whole genome scanning identifies genotypes associated with recurrence and metastasis in prostate cancer," *Human Molecular Genetics* 13(13):1303-1313 (2004).
Patience, et al., "Human Endogenous Retrovirus Expression and Reverse Transcriptase Activity in the T47D Mammary Carcinoma Line," *J. Virol.* 70(4):2654-2657 (Apr. 1996).
Perner, et al., "*TMPRSS2-ERG* Fusion Prostate Cancer: An Early Molecular Event Associated With Invasion," *Am. J. Surg. Pathol.* 31(6):882-888 (Jun. 2006).
Petrovics, et al., "Frequent overexpression of *ETS*-related gene-1 (*ERG1*) in prostate cancer transcriptome," *Oncogene* 24:3847-3852 (2005).
Pflueger, et al.,"*N-myc Downstream Regulated Gene 1 (NDRG1)* is Fused to *ERG* in Prostate Cancer," *Neoplasia* 11(8):804-811 (Aug. 2009).
Price, et al., "Toremifene for the Prevention of Prostate Cancer in Men With High Grade Prostatic Intraepithelial Neoplasia: Results of a Double-Blind, Placebo Controlled, Phase IIB Clinical Trial," *J. Urol.* 176:965-970 (2006).
Rabbitts, et al., "Chromosomal translocations in human cancer," *Nature* 372:143-149 (Nov. 1994).
Rao, et al., "*erg*, a Human *ets*-Related Gene on Chromosome 21: Alternative Splicing, Polyadenylation, and Translation," *Science* 237:635-639 (Aug. 1987).
Reddy, et al., "The *erg* gene: A human gene related to the *ets* oncogene," *Proc. Natl. Acad. Sci. USA* 84:6131-6135 (Sep. 1987).
Rhodes, et al., "ONCOMINE: A Cancer Microarray Database and Integrated Data-Mining Platform," *Neoplasia* 6(1):1-6 (Jan./Feb. 2004).
Rickman, et al., "SLC45A3-ELK4 Is a Novel and Frequent Erythroblast Transformation-Specific Fusion Transcript in Prostate Cancer," *Cancer Res.* 69(7):2734-2738 (Apr. 2009).
Rosenwald, et al., "The proliferation gene expression signature is a quantitative integrator of oncogenic events that predicts survival in mantle cell lymphoma," *Cancer Cell* 3:185-197 (Feb. 2003).
Rowley, "A New Consistent Chromosomal Abnormality in Chronic Myelogenous Leukaemia identified by Quinacrine Fluorescence and Giemsa Staining," *Nature* 243:290-293 (Jun. 1973).
Rowley, "Chromosome translocations: dangerous liaisons revisited," *Nature Reviews, Cancer* 1:245-250 (Dec. 2001).
Rubin, et al., "Overexpression, Amplification, and Androgen Regulation of TPD52 in Prostate Cancer," *Cancer Res.* 64:3814-3822 (Jun. 2004).
Rubin, et al., "Bioinformatics approach leads to the discovery of the TMPRSS2:ETS gene fusion in prostate cancer," *Laboratory Investigation* 86:1099-1102 (2006).
Schröder, "Re: Duplication of the Fusion of TMPRSS2 to ERG Sequences Identifies Fatal Human Prostate Cancer, Attard, et al.," Expert's Summary, *European Urology* 53:208-211 (2008).
Schwartz, et al., "Gene Expression in Ovarian Cancer Reflects Both Morphology and Biological Behavior, Distinguishing Clear Cell from Other Poor-Prognosis Ovarian Carcinomas," *Cancer Res.* 62:4722-4729 (Aug. 2002).
Seaton-Rodgers, "Translocation," *Nature Reviews, Cancer* 7:638 (Sep. 2007).
Shi, et al., "Molecular Alterations Associated With LNCaP Cell Progression to Androgen Independence," *The Prostate* 60:257-271 (2004).
Slamon, et al., Human Breast Cancer: Correlation of Relapse and Survival with Amplification of the HER-2/*neu* Oncogene, *Science* 235:177-182 (Jan. 1987).

Smith, et al., "Expression profiling of EWS/FLI identifies NKX2.2 as a critical target gene in Ewing's sarcoma," *Cancer Cell* 9:405-416 (May 2006).

Soller, et al., "Confirmation of the High Frequency of the TMPRSS2/ERG Fusion Gene in Prostate Cancer," *Genes, Chromosomes & Cancer* 45:717-719 (2006).

Sotiriou, et al., "Breast cancer classification and prognosis based on gene expression profiles from a population-based study," *PNAS* 100(18):10393-10398 (Sep. 2003).

Stauffer, et al., "Digital expression profiles of human endogenous retroviral families in normal and cancerous tissues," Cancer Immunity 4:1-18 (2004).

Stavenhagen, et al., "An Ancient Provirus Has Imposed Androgen Regulation on the Adjacent Mouse Sex-Limited Protein Gene," *Cell* 55:247-254 (Oct. 1988).

Stefford, et al., "The use of multicolor fluorescence technologies in the characterization of prostate carcinoma cell lines: a comparison of multiplex fluorescence in situ hybridization and spectral karyotyping data," *Cancer Genetics and Cytogenetics* 124:112-121 (2001).

Suzukawa, et al., "Identification of a Breakpoint Cluster Region 3' of the Ribophorin I Gene at 3q21 Associated With the Transcriptional Activation of the *EVI1* Gene in Acute Myelogenous Leukemias With inv(3)(q21q26)," *Blood* 84(8):2681-2688 (Oct. 1994).

Takaha et al., "High Mobility Group Protein I(Y): A Candidate Architectural Protein for Chromosomal Rearrangements in Prostate Cancer Cells," *Cancer Res.* 62:647-651 (Feb. 2002).

Thalmann, et al., "Androgen-independent Cancer Progression and Bone Metastasis in the LNCaP Model of Human Prostate Cancer," *Cancer Res.* 54:2577-2581 (May 1994).

Tian, et al., "The Role of the Wnt-Signaling Antagonist DKK1 in the Development of Osteolytic Lesions in Multiple Myeloma," *N. Engl. J. Med.* 349(26):2483-2494 (Dec. 2003).

Tomlins, et al., "Distinct classes of chromosomal rearrangements create oncogenic ETS gene fusions in prostate cancer," *Nature* 448:595-599 (Aug. 2007).

Tomlins, et al., "Integrative Biology of Prostate Cancer Progression," *Annu. Rev. Pathol. Mech. Dis.* 1:243-271 (2006).

Tusher, et al., "Significance analysis of microarrays applied to the ionizing radiation response," *PNAS* 98(9):5116-5121 (Apr. 2004).

Vaarala, et al., "The *TMPRSS2* Gene Encoding Transmembrane Serine Protease is Overexpressed in a Majority of Prostate Cancer Patients: Detection of Mutated TMPRSS2 Form in a Case of Aggressive Disease," *Int. J. Cancer* 94:705-710 (2001).

Van Bokhoven, et al., "Spectral Karyotype (SKY) Analysis of Human Prostate Carcinoma Cell Lines," *The Prostate* 57:226-244 (2003).

Vasselli, et al., "Predicting survival in patients with metastatic kidney cancer by gene-expression profiling in the primary tumor," *PNAS* 100(12):6958-6963 (Jun. 2003).

Velasco, et al., Identification and Validation of Novel Androgen-Regulated Genes in Prostate Cancer, *Endocrinology* 145(8):3913-3924 (2004).

Walker, et al., "Predication of Gene Function by Genome-Scale Expression Analysis: Prostate Cancer-Associated Genes," *Genome Res.* 9:1198-1203 (Dec. 1999).

Wang, et al., "Expression of Variant TMPRSS2/ERG Fusion Messenger RNAs Is Associated with Aggressive Prostate Cancer," *Cancer Res.* 66(17):8347-8351 (Sep. 2006).

Wang, et al., "Gene-expression profiles to predict distant metastasis lymph-node-negative primary breast cancer," *The Lancet* 365:671-679 (Feb. 2005).

Wang-Johanning, et al., "Quantitation of HERV-K env gene expression and splicing in human breast cancer," *Oncogene* 22:1528-1535 (2003).

Watson, et al., "Cytogenetically balanced translocations are associated with focal copy number alterations," Hum. Genet. 120:759-805 (2007).

Weigle, et al.,"*D-PCa-2*: A Novel Transcript Highly Overexpressed in Human Prostate and Prostate Cancer," *Int. J. Cancer* 109:882-892 (2004).

Welsh, et al., "Analysis of Gene Expression Identifies Candidate Markers and Pharmacological Targets in Prostate Cancer," *Cancer Res.* 61:5974-5978 (Aug. 2001).

Wieser, et al., "Rearrangements of Chromosome Band 3q21 in Myeloid Leukemia," *Leukemia & Lymphoma* 43:59-65 (2002).

Wigle, et al., "Molecular Profiling of Non-Small Cell Lung Cancer and Correlation with Disease-free Survival," *Cancer Research* 62:3005-3008 (Jun. 2002).

Williams, et al., "CpG-island fragments from the HNRPA2B1/CBX3 genomic locus reduce silencing and enhance transgene expression from the hCMV promoter/enhancer in mammalian cells," *BMC Biotechnology* 5(17):1-9 (2005).

Xu, et al., "Identification and Characterization of Prostein, a Novel Prostate-specific Protein," *Cancer Res.* 61:1563-1568 (Feb. 2001).

Yoshimoto, et al., "Three-Color Fish Analysis of TMPRSS2/ERG Fusions in Prostate Cancer Indicated That Genomic Microdeletion of Chromosome 21 Associated with Rearrangement," *Neoplasis* 8(6):465-469 (Jun. 2006).

Zhan, et al., "Global gene expression profiling of multiple myeloma, monoclonal gammopathy of undetermined significance, and normal bone marrow plasma cells," *Blood* 99(5):1745-1757 (Mar. 2002).

GenBank Accession No. NP004440, 1987.
GenBank Accession No. P11308, 1989.
GenBank Accession No. M17254, 1983.
GenBank Accession No. AAC51784, 1996.
GenBank Accession No. O15393, 1998.
GenBank Accession No. U75329, 1997.
GenBank Accession No. ALI163285, 2000.

\* cited by examiner

IDENTIFICATION AND TREATMENT OF ESTROGEN RESPONSIVE PROSTATE TUMORS

CROSS REFERENCE TO RELATED APPLICATIONS

The present application claims priority to and the benefit of U.S. provisional application 60/935,299, filed on Aug. 3, 2007 which is hereby incorporated herein by reference in its entirety.

STATEMENT OF GOVERNMENT SUPPORT

The work leading to this invention was supported by the U.S. Government under NIH Grant No. R01AG21404 provided by the Department of Health and Human Services. The U.S. Government therefore has certain rights in the invention.

FIELD OF THE INVENTION

The present invention is concerned with methods of identifying prostate cancer cells that have a specific chromosomal rearrangement and the treatment of patients with tumors having cells of this type. In particular, the invention is directed to the treatment of patients having prostate tumors characterized by a TMPRSS2-ERG chromosomal rearrangement using agonists of the estrogen beta receptor and/or antagonists of the estrogen alpha receptor.

BACKGROUND

Prostate cancer remains a major public health challenge, with an anticipated 219,000 new cases to be diagnosed this year in the United States and 27,000 deaths expected from the disease (Jemal, et al. *CA Cancer J. Clin.* 57:43-66 (2007)). The absence of effective treatment for advanced disease reflects, in part, the lack of a detailed understanding of the molecular pathogenesis of prostate cancer. A striking recent discovery, however, indicates that 40-70% of men diagnosed with prostate cancer harbor an acquired chromosomal translocation that results in the fusion of the promoter region of the Transmembrane protease, serine 2 (TMPRSS2) gene to the coding region of members of the erythroblast transformation specific (ETS) family of transcription factors, most commonly V-ets erythroblastosis virus E26 oncogene homolog (avian) (ERG) (Tomlins, et al., *Cancer Res.* 66:3396-400 (2006); Tomlins, et al., *Science* 310:644-648 (2005)). TMPRSS2-ERG fusion prostate cancers appear to have a more aggressive natural clinical history (Demichelis, et al., *Oncogene* 2007)). The downstream effects of TMPRSS2-ERG have yet to be identified, and the mechanism by which TMPRSS2-ERG contributes to the pathogenesis of prostate cancer is entirely unknown. A significant challenge is therefore to identify therapeutic strategies for the manipulation of TMPRSS2-ERG function in prostate cancer cells.

SUMMARY OF THE INVENTION

The present invention is based, in part, upon studies in which gene expression profiling was used to define a signature of TMPRSS2-ERG activity in primary prostate cancer specimens. The results suggest that tumors carrying cells with this rearrangement represent a distinct subclass that grow in response to estrogen. Further studies indicated that growth of these tumors is stimulated by agonists of the estrogen alpha receptor (ER$\alpha$) and by antagonists of the estrogen beta receptor (ER$\beta$). In contrast, growth is inhibited by agonists of ER$\beta$ and antagonists of ER$\alpha$.

In its first aspect, the invention is directed to a method of treating a patient for a prostate tumor in which cells from the tumor are assayed to determine whether they carry a TMPRSS2/ERG chromosomal rearrangement. If such a rearrangement is present, then the patient is administered a selective estrogen receptor modulator (SERM) chosen from: a) a compound that is a much stronger antagonist of ER$\alpha$ an ER$\beta$ in prostate cells; and/or b) a compound that is a much stronger agonist of ER$\beta$ than ER$\alpha$ in prostate cells. The term "much stronger" refers to a SERM that is at least "preferential" in its action, which for the purposes of the present invention, means either that: a) in a standard assay of ER$\alpha$ and ER$\beta$ activity, the amount of SERM needed to decrease ER$\alpha$ activity by 50% is less than one half of the amount needed to decrease ER$\beta$ activity by 50%; or that: b) the amount of SERM needed to increase ER$\beta$ activity by 50% is less than one half the amount needed to increase ER$\alpha$ activity by 50%. Preferably, the SERM is "specific" in its action which, for the purposes of the present invention, means either that: a) in a standard assay of ER$\alpha$ and ER$\beta$ activity, the amount of SERM needed to decrease ER$\alpha$ activity by 50% is less than one tenth of the amount needed to decrease ER$\beta$ activity by 50%; or that: b) the amount of SERM needed to increase ER$\beta$ activity by 50% is less than one tenth the amount needed to increase ER$\alpha$ activity by 50%. Ideally, the SERM should be "highly specific" which is defined as a compound that either: a) acts as an antagonist of ER$\alpha$ but exhibits no detectable ER$\beta$ antagonist activity at the dosages administered to a patient; or b) acts as an agonist of ER$\beta$ but exhibits no detectable ER$\alpha$ agonist activity at the dosages administered to a patient. SERMs that may be used in the method include: clomofene; bazedoxifene; lasofoxifene; ormeloxifene; arzoxifene; and preferably, 17$\beta$-estradiol; fulvestrant; resveretrol; diarylpropionitrile; or tamoxifen.

The dosage of SERM administered to a patient will depend upon the particular compound being used and on clinical factors. However, in general, it is expected that patients will be given SERMs orally at a dose of 0.2-40 mg per kg body weight per day and preferably 0.2-5 mg per kg body weight per day. If given by injection, these dosages will be reduced by between 10 and 95%.

Any method of determining whether cells carry a TMPRSS2/ERG chromosomal rearrangement may be used in conjunction with the treatment method described above. However, the fluorescence in situ hybridization (FISH) assay and the gene expression profiling procedures discussed in the Examples section are preferred.

In a more general aspect, the invention is directed to a method of treating a patient for prostate cancer by administering: a SERM that acts as a preferential, specific or highly specific ER$\alpha$ antagonist; b) a SERM that acts as a preferential, specific or highly specific ER$\alpha$ antagonist; or c) both. The terms "preferential," "specific" and "highly specific" have the meanings discussed above. In general, the more specific that a SERM is in its action as an ER$\alpha$ antagonist and/or ER$\beta$ agonist, the more that it is preferred for use in treating patients. This method differs from the one described above in that an assay is not necessarily performed to confirm the presence of a TMPRSS2/ERG chromosomal rearrangement prior to or during therapy. It therefore has the advantage of convenience but the disadvantage that there is a greater chance of a patient not responding. The same SERMs and dosages recited above may be used. A positive response will be evidenced by a clinical improvement in a patient, e.g., a decrease in tumor mass or a slowing of tumor growth. If this occurs, the therapy should be continued. If there is no clinical improvement, this is an indication that the patient's cancer cells probably do not have the TMPRSS2/ERG chromosomal rearrangement and the therapy should be stopped.

The invention also encompasses a method of testing a compound to determine whether it is likely to promote or inhibit the growth of prostate cells carrying a TMPRSS2/ERG chromosomal rearrangement by determining its activity with respect to ERα and ERβ. If the compound acts preferentially as an agonist of ERα (i.e., it has a greater agonistic effect on ERα than ERβ) or preferentially as an antagonist of ERβ (i.e., it has a greater antagonistic effect on ERβ than ERα), it may be concluded that the compound probably promotes growth and is something that prostate cancer patients should avoid. If the compound acts preferentially as an antagonist of ERα (i.e., it has a greater antagonistic effect on ERα than ERβ) or preferentially as an agonist of ERβ (i.e., it has a greater agonistic effect on ERβ than ERα), it may be concluded that the compound probably inhibits growth and is something that may have use in the treatment of patients.

In another aspect, the invention encompasses a method of determining whether a sample of "test" prostate cells exhibit a gene expression profile characteristic of the presence of a TMPRSS2/ERG chromosomal rearrangement. The method involves assaying the cells to determine the degree of expression of one or more genes selected from the group consisting of: RAB27A; ALOX15B; CSDC2; FOXF2; KLHL21; GRK1; PNLIPRP2; AMELX; HPS1; NEUROD1; AADAC; AQP2; RGS7; METTL7A; CCR1; ITGAD; TRO; PROM1; ADH5; MPPED2; RAB30; PLA2G7; ZNF3; TPP2; DDEF2; XRCC5; TLE1; TWIST1; ABCC8; ERG; ECE1; CACNA1D; GP1BB; RFX1; EIF4G3; MAP7; CADPS; ARHGAP29; DBN1; KCNN2; HDAC1; KHDRBS3; SH3YL1; EIF5; SIPA1L1; AMPD3; PTPRK; RPP38; PCDHGB7; CPSF6; PEX10; SEPT9; ALDH18A1; TFDP1; PSMD13; CRISP3; PFTK1; PDE9A; RAGE; BAG5; LRP1; THUMPD1; SAFB; GHR; BMPR1B; COL9A2; MYO6; ARHGDIB; PRKAR1B; KNS2; PTK7; OCLN; MLXIP; KIAA0247; RGS10; UBE2G1; PRKCBP1; MAP3K5; MAP2K5; PGD; TBP; NCOA1; MTA1; SMARCD1; SNRPB2; UGDH; and NDUFS5. These are all genes that have been fully characterized and that are well known in the art (see e.g., NCBI Entrez database).

A gene expression profile characteristic of the presence of a TMPRSS2/ERG chromosomal rearrangement is evidenced by: a) a decrease in the expression of one or more of the following genes in the test prostate cells relative to expression in control prostate cells: RAB27A; ALOX15B; CSDC2; FOXF2; KLHL21; GRK1; PNLIPRP2; AMELX; HPS1; NEUROD1; AADAC; AQP2; RGS7; METTL7A; CCR1; ITGAD; TRO; PROM1; ADH5; MPPED2; and/or b) an increase in the expression of one or more of the following genes in the test prostate cells relative to control prostate cells: RAB30; PLA2G7; ZNF3; TPP2; DDEF2; XRCC5; TLE1; TWIST1; ABCC8; ERG; ECE1; CACNA1D; GP1BB; RFX1; EIF4G3; MAP7; CADPS; ARHGAP29; DBN1; KCNN2; HDAC1; KHDRBS3; SH3YL1; EIF5; SIPA1L1; AMPD3; PTPRK; RPP38; PCDHGB7; CPSF6; PEX10; SEPT9; ALDH18A1; TFDP1; PSMD13; CRISP3; PFTK1; PDE9A; RAGE; BAG5; LRP1; THUMPD1; SAFB; GHR; BMPR1B; COL9A2; MYO6; ARHGDIB; PRKAR1B; KNS2; PTK7; OCLN; MLXIP; KIAA0247; RGS10; UBE2G1; PRKCBP1; MAP3K5; MAP2K5; PGD; TBP; NCOA1; MTA1; SMARCD1; SNRPB2; UGDH; and NDUFS5. The test prostate cells are preferably derived from a tumor and the control prostate cells are preferably either prostate cells known to not be cancerous or cancerous prostate cells known to not have the TMPRSS2/ERG chromosomal rearrangement. In order to conclude that the rearrangement is present, the number of genes that are decreased in expression and the number that are increased in expression in the test prostate cells should total at least 20, and preferably at least 40 or 80. The preferred method of assay is through the use of microarray plates.

DETAILED DESCRIPTION OF THE INVENTION

The present invention is based upon the discovery that the growth of prostate cancer cells having a TMPRSS2/ERG chromosomal rearrangement is inhibited by agents that act as agonists of ERβ or as antagonists of ERα. In contrast, agents that act as agonists of ERα or as antagonists of ERβ have the opposite effect, i.e., they promote cancer cell growth. The conclusion that may be drawn from this is that an ideal therapeutic agent would be one that acts exclusively as an agonist of ERβ (i.e. with no effect on ERα) and/or exclusively as an antagonist of ERα. Cancerous prostate cells that do not have the TMPRSS2/ERG rearrangement are unlikely to respond to agents that act at the estrogen receptors.

Sequences

Unless otherwise indicated expressly or by context, the therapeutic and diagnostic methods of the present invention are for use in humans. Thus, genes and proteins referred to herein in connection with gene profiling, diagnostic assays and treatments, are from or for humans even though experiments may have been performed in cells, mice etc. More specific information for certain genes may be found in the following references:

Human ERG: Human ERG is found on chromosome 21, the relevant sequence of which is found in GenBank accession numbers: NC_000021.7; NT_011512.10 and NT_086913.1 (see also Hattori, et al. *Nature* 405: 311-319 (2000)). The gene is located at 38,675,671 bp from the pter-38,955,488 bp from the pter (279,817 total bp; minus strand orientation).

The human ERG protein sequence may be found at GenBank accession no. NP04440 (Swiss Protein acc. no. P11308) and the cDNA sequence may be found at GenBank accession no. M17254 (see also Rao, et al., *Science* 237:635-639 (1987)).

Human TMPRSS2: This gene is also found on chromosome 21 at 41,750,797 bp from the pter-41,801,948 bp from the pter (51,151 total bp; minus strand orientation; same chromosomal sequence accession nos. as for ERG; see also GenBank accession no. AL163285).

The human TMPRSS2 protein sequence may be found at GenBank accession no. AAC51784 (Swiss Protein accession no. 015393)) and the corresponding cDNA at GenBank accession no. U75329 (see also, Paoloni-Giacobino, et al., *Genomics* 44:309-320 (1997)).

SERMs

All of the SERMs described herein are known in the art and, in some cases, are available commercially for the treatment of patients, especially patients with breast cancer. Unless otherwise indicated, it will be understood that any pharmaceutically acceptable form of these compounds, including any pharmaceutically acceptable salts, may be used in the treatment of patients. In general, the SERMs will be administered in a dosage range of 0.1-40 mg/kg body weight per day, and preferably at between 0.2 and 5 mg/kg/day. Non-limiting examples of dosages that may be used include: 17 β-estradiol at 0.25-2 mg per day orally; fulvestrant at 10-40 mg per day im or 300-600 mg per day orally; tamoxifen at 5-40 mg per day orally; and diarylpropionitrile or basedoxifene at 20-400 mg per day orally.

Assays for Chromosomal Rearrangements

In order to carry out assays to determine whether a TMPRSS2/ERG fusion has occurred, prostate cells must first be obtained. This may occur as the result of a biopsy or during surgery for a prostate tumor. Any assay may then be used to determine whether cells are present having a rearrangement of the type discussed above. One preferred assay is the fluorescence in situ hybridization (FISH) assay discussed in the Examples section and described by Perner, et al. (*Cancer Res.* 66:8337-8341 (2006)). As an alternative, the polymerase chain reaction may be used to amplify sequences in regions that would indicate that a fusion has occurred. Specific primers that can be used in carrying out PCR are have been described in the art. However, one of skill in the art could readily construct primers based upon known chromosomal sequences and successfully employ other protocols in connection with the invention.

It has also been discovered that prostate cells with the TMPRSS2/ERG chromosomal rearrangement exhibit a unique set of genes that are expressed at an increased or decreased level compared to expression in prostate cells that do not have the rearrangement. Thus, a gene profile indicative of the rearrangement can be determined using assays on microarray plates. Although the plates and procedures described in the Examples section can be used, alternatives are also available and compatible with the invention.

Many reviews have been written detailing methods for making microarrays and for carrying out assays (see, e.g., Bowtell, *Nature Genetics Suppl.* 21:25-32 (1999); Constantine, et al., *Life Sci. News* 1:11-13 (1998); Ramsay, *Nature Biotechnol.* 16:40-44 (1998)). In addition, patents have issued describing techniques for producing microarray plates, slides and related instruments (U.S. Pat. No. 6,902, 702; U.S. Pat. No. 6,594,432; U.S. Pat. No. 5,622,826) and for carrying out assays (U.S. Pat. No. 6,902,900; U.S. Pat. No. 6,759,197). The two main techniques for making plates or slides involve either polylithographic methods (see U.S. Pat. No. 5,445,934; U.S. Pat. No. 5,744,305) or robotic spotting methods (U.S. Pat. No. 5,807,522). Other procedures may involve inkjet printing or capillary spotting (see, e.g., WO 98/29736 or WO 00/01859).

The substrate used for microarray plates or slides can be any material capable of binding to and immobilizing oligonucleotides, including plastic, metals such a platinum, and glass. Many schemes for covalently attaching oligonucleotides have been described and are suitable for use in connection with the present invention (see, e.g., U.S. Pat. No. 6,594, 432). The immobilized oligonucleotides should be, at a minimum, 20 bases in length and should have a sequence exactly corresponding to a segment in the gene targeted for hybridization.

Pharmaceutical Compositions

The SERMs described herein may be incorporated into pharmaceutical compositions in accordance with methods that are standard in the art (see e.g., *Remington's Pharmaceutical Sciences*, Mack Publishing Co., (1990)). Formulations may be designed for delivery by any of the routes commonly used in the art, with preparations designed for oral administration being generally preferred. For oral compositions, e.g. tablets or capsules, the SERMs should typically be present in an amount of between 0.5 and 500 mg per unit dosage form (i.e., in each tablet, capsule, etc.). Drugs may also be given parenterally, in which case the dosage will typically be reduced by at least 50% and as much as 95%.

SERMs may be used in conjunction with any of the vehicles and excipients commonly employed in pharmaceutical preparations including water, salt solutions, alcohols, gum arabic, vegetable oils, benzo-alcohols, polyethylene glycol, gelatin, carbohydrates such as lactose, amylase, or starch; magnesium stearate; talc; salycic acid; paraffin; fatty acid esters; polymers; etc. The pharmaceutical preparations can be sterilized and, if desired, mixed with auxiliary agents such as: dispersants; lubricants; preservatives; stabilizers; wetting agents; emulsifiers; salts for influencing osmotic pressure; buffers; coloring agents; flavoring agents; and/or aromatic substances.

Solutions, particularly solutions for injection, can be prepared using water or physiologically compatible organic solvents such ethanol, 1,2-propylene glycol; polygycols; dimethylsulfoxides; fatty alcohols; triglycerides; partial esters of glycerine; and the like. The preparations can be made using conventional techniques and may include sterile isotonic saline, water, 1,3-butanediol, ethanol, 1,2-propylene glycol, polygycols mixed with water, ringers Ringer's solution etc.

Dosage Forms and Routes of Administration

The present invention is compatible with any route of administration including oral, peroral, internal, rectal nasal, lingual, transdermal, intravenous, intraarterial, intramuscular, intraperitoneal, intracutaneus and subtaneous routes. Dosage forms that may be used include tablets, capsules, powders, aerosols, suppositories, skin patches, parenterals, sustained release preparations and oral liquids, including suspensions solutions and emulsions. The most preferred routes for administration are oral and by injection. If desired, compositions, particularly compositions for injection, may be freeze-dried and lyophilizates reconstituted before administration. Dosage forms may include SERMs as the sole active ingredient or may include other active agents as well. All dosage forms may be prepared using methods that are standard in the art and that are taught in reference works such as *Remington's Pharmaceutical Sciences* (Osol, A, ed., Mack Publishing Co. (1990)).

Examples

The present example describes experiments in which we used the cDNA-based microarray technology, DNA-mediated Annealing, Selection, Ligation and Extension (DASL) for the analysis of archival samples from 455 primary prostate tumors. The samples were derived from a Swedish Watchful Waiting cohort (1987 to 1999) and US based Physicians Health Study cohort (1983-2003). A custom array was designed for the study to interrogate ~6000K genes involved in prostate cancer progression.

An 87-gene expression signature was identified, distinguishing TMPRSS2-ERG fusion prostate cancer as a discrete molecular entity. Computational analysis suggested that this fusion signature was associated with estrogen receptor signaling. Functional studies demonstrated regulation of the TMPRSS2-ERG fusion transcript by estrogenic compounds. The results indicate that TMPRSS2-ERG fusion prostate cancer is a distinct molecular subclass. We also identified and validated a previously unrecognized mechanism for regulation of TMPRSS2-ERG expression, even in the absence of a functional androgen receptor, which has broad implications in the treatment of prostate cancer.

I. Methods

Patient Population

Swedish Cohort: The population-based Swedish Watchful Waiting Cohort consists of 1,256 men with localized prostate cancer (clinical stage T1-T2, Mx, N0) and a prospective follow-up time of up to 30 years. Regional Cohort (N=240) includes men diagnosed at University Hospital in Örebro (1977 to 1991) (6-8) and from four centers in the Southeast region of Sweden, Kalmar, Norrköping, Linköping, and Jonköping (1987 to 1999). A total of 388 prostate cancer patients were included in the study.

Physician Health Study (PHS) Prostatectomy Confirmation Cohort: This group included 116 US men diagnosed with incidental prostate cancer between 1983 and 2003 and treated by radical prostatectomy as primary therapy. The men were participants in an ongoing randomized trial in the primary prevention of cancer and cardiovascular disease.

DASL Array Design

We designed a set of 4 DAPS for the discovery of molecular signatures relevant to prostate cancer. We prioritized informative genes, i.e., genes having larger variation across the samples in previously generated microarray data sets, including 24 studies, 2,149 samples, and 15 tissue types. The top ranked genes sufficiently covered most of the genes in known biological pathways. To ensure that prostate cancer related genes were included in the DAP, we performed a meta-analysis of previous microarray data sets from the Oncomine Database (Rhodes, et al., *Neoplasia* 6:1-6 (2004)) and included significant genes from that list. The final array consisted of 6,144 genes (6K DAP).

Sample Processing and DASL

Three biopsy cores (0.6 μm each) were used for high through-put 96-well RNA extraction using Trizol LS reagent (Invitrogen). The quality of the RNA was determined using RPL13A Bibikova, et al., *Am. J. Pathol.* 165:1799-1807 (2004)). 400 ng cDNA was used for DASL (Illumina).

Fusion Status Determination

Fusion status was determined by ERG break-apart FISH assay (Pemer, et al., *Cancer Res.* 66:8337-8341 (2006)) and QPCR (for cases not assessable by FISH). An aliquot of the RNA used for DASL was used for QPCR. cDNA was synthesized as above. TMPRSS2-ERG fusion product was determined using SYBR green assay (Qiagen) with TMPRSS2-ERG_f and TMPRSS2-ERG_r primers (Tomlins, et al., *Science* 310:644-648 (2005)). RPL13A was used for normalization. For estrogen experiments, cDNA was synthesized using the Omniscript RT kit (Qiagen) and HMBS was used for normalization. Relative quantitation was carried out using the comparative $C_t$ method.

Computational Analysis

The DASL array data was pre-processed and the selection of genes associated with fusion was carried out on the Swedish cohort. A Two-sided T-test was applied on each gene on 10 splits of 10-fold cross-validation. Genes selected were identified as being significantly associated with TMPRSS2-ERG fusion as determined by FISH or QRT-PCR at least in 50% of the iterations.

Cell Lines

The prostate cancer cell lines NCI-H660 and VCaP were maintained according to ATCC instructions. The cells were hormone-deprived by culture for three days in their respective phenol red-free media (for NCI-H660 without E2 and hydrocortisone) supplemented with 5% CDT-FBS (Invitrogen). Cells were challenged with hormones or vehicle for 12, 24 or 48 hours.

Hormonal Treatments

17β-Estradiol (Sigma), alpha-E2 (Sigma), PPT (Tocris) and DPN (Tocris) were dissolved in 100% EtOH, raloxifene (Sigma), tamoxifen (Sigma) and fulvestrant (Sigma) were dissolved in DMSO. Reagents were used at a final concentration of $10^{-8}$M.

Cell Growth Assays

NCI-H660 cells were seeded in a 96-well plate (~$5 \times 10^3$ cells/well) and stimulated with hormone or vehicle alone. Relative cell number was determined before (time 0 used for normalization) and after stimulation (2, 3, 6, 8, 10, 12 d) using the Cell Titer-Glo luminescent assay (Promega).

Chromatin Immunoprecipitation (ChIP)

ChIP was performed as previously described by Carroll et al. Carroll, et al., *Nat. Genet.* 38:1289-1297 (2006)). Briefly, NCI-H660 cells were hormone-deprived by culture for 3 days in phenol red-free medium (Cellgro) supplemented with 5% CDT-FBS (Invitrogen), lacking E2 and hydrocortisone. Cells were challenged with E2 or vehicle for 60 min, and chromatin was crosslinked using 1% formaldehyde. For primers and ER binding sites tested.

Western Blotting

Whole cell extracts were prepared in RIPA buffer (50 mM Tris (pH 7.5), 150 mM NaCl, 2 mM sodium orthovanadate, 0.1% Nonidet P-40, 0.1% Tween 20) with 1× Complete protease inhibitor cocktail (Roche). Protein concentration was determined using the Bio-Rad DC protein assay. 20 kg of total protein was loaded on NuPAGE 4-12% Tris-Bis gels (Invitrogen) and transferred to Immobilon-P PVDF membrane (Millipore). Primary antibodies: monoclonal anti-ERα (1:100, NeoMarkers), monoclonal anti-ERβ (1:200, GeneTex). Secondary antibody: Peroxidase-conjugated anti-mouse (1:8000, Amersham). Signal was detected using ECL Western Blotting Analysis System (Amersham).

Transfection Assays

VCaP cells were transiently transfected with ERβ containing plasmid using Lipofectamine2000 (Invitrogen) for 6 h. Transfection medium was removed after 6 h, cells were washed in PBS twice, and phenol red-free DMEM (Cellgro) supplemented with 5% CDT-FBS (Invitrogen) was added. Cells were challenged with hormones or vehicle 48 hours after transfection. NCI-H660 cells were transiently transfected with smart pool siRNA against ERβ (Dharmacon).

II. Results

DASL Based Expression Array Profiling of Archival Tissue

We developed a novel high through-put method to profile the expression of 6,144 genes in archival tissue specimens. 504 primary prostate cancer specimens were obtained from two cohorts: the Swedish Watchful Waiting Clinical Trial Cohort (n=388) and the PHS cohort from the United States (14) (n=116). High quality expression data was obtained from 472 of the samples (93.6%). Raw data are available at www-.broad.mit.edu/cancer/pubs/prostate_DASL.

Fusion Status Determination

In order to define a gene expression signature of TMPRSS2-ERG fusion cancer, we performed fluorescence in situ hybridization (FISH) on the 472 prostate cancer cases for which tissue was available, using quantitative PCR in the cases where FISH results were not conclusive (455 cases were overall successfully annotated). These studies indicated that 17.5% of the Swedish Watchful Waiting cases (diagnosed as incidental findings following transurethral prostate resections for benign prostatic hypertrophy) were positive for the fusion. 40.6% of the PHS cases (a majority of whom were diagnosed through PSA screening) were positive for TMPRSS2-ERG.

Molecular Signature of TMPRSS2-ERG Fusion

We next asked whether a gene expression correlate of TMPRSS2-ERG could be identified. Two thirds of the Swedish cohort (n=235) was used as a training set, and the remaining one third of the Swedish samples (n=119) was reserved as a validation set. 170 genes were significantly correlated with TMPRSS2-ERG fusion status after correction for multiple hypotheses testing (false discovery rate<0.01). This result suggests that TMPRSS2-ERG cancers are indeed molecularly distinct from the fusion negative cases. Next, a gene expression-based classifier built on the training data was then applied without modification to the 119 Swedish validation samples. The Area Under the ROC Curve (AUC) of this predictor was 79.3% (p<0.001), again demonstrating that TMPRSS2-ERG positive prostate cancers are molecularly distinct from fusion-negative tumors. After validation, we combined all 354 Swedish Watchful Waiting cases to build a robust model that included 87 genes. We confirmed the TMPRSS2-ERG signature on the PHS cases and 4 other prostate cancer expression array profiles.

Pathway Analysis of the TMPRSS2-ERG Signature

The next challenge was to attempt to understand the nature of the final TMPRSS2-ERG signature, comprised of 87 genes. To do this, we undertook 2 computational strategies: i) the Connectivity Map (Lamb, et al., Science 313:1929-1935 (2006)), an approach for identifying similarities between signatures of interest and the gene expression consequence of small-molecule drug treatment, and ii) the Molecular Concepts Map (MCM) (Tomlins, et al., Nat. Genet. 39:41-51 (2007); Rhodes, et al., Neoplasia 9:443-454 (2007)), a system for comparing a signature to a database of protein-protein interaction networks, microarray profiles, and other genomic information.

A common hypothesis emerged from each of these analyses, namely a relationship between the TMPRSS2-ERG signature and estrogen receptor signaling. The MCM and the Connectivity Map showed evidence of anti-correlation between the tumor tissue-derived TMPRSS2-ERG signature and the gene expression profile of MCF7 cells treated with the anti-estrogen fulvestrant. Similarly, the Connectivity Map showed similarity between the TMPRSS2-ERG signature and the estrogen receptor beta (ERβ) agonists resveratrol and genistein. The MCM identified several estrogen-related concepts Tomlins, et al., Nat. Genet. 39:41-51 (2007); Rhodes, et al., Neoplasia 9:443-454 (2007)), for example the concept for fulvestrant was also identified by the MCM. The MAP kinase interacting kinase 2 (MKNK2) HPRD interaction set concept was significantly enriched. MKNK2 selectively associates with the ligand-binding domain of ERβ and is believed to activate ERβ through phosphorylation in a ligand-independent manner (Slentz-Kesler, et al., Genomics 69:63-71 (2000)). While these computational analyses do not identify definitive connections between TMPRSS2-ERG fusion and estrogen signaling, they suggested a hypothesis that could be tested functionally.

Validation of the Role of Estrogens in TMPRPSS2-ERG Fusion

Therefore, to investigate the selective role of estrogen (E2) and ER-mediated pathways in TMPRSS2-ERG fusion tumors, we performed a series of functional studies in vitro. The NCI-H660 prostate cancer cell line harbors a transcriptionally active homozygous TMPRSS2-ERG fusion and expresses both estrogen receptor alpha (ERα) and ERβ in the absence of an androgen receptor (AR) (Mertz, et al., Neoplasia 9:200-206 (2007)), which normally regulates wild-type TMPRSS2 expression (Lin, et al., Cancer Res 59:4180-41844 (1999)). Consequently, ERG expression is not androgen-regulated in this cell line Mertz, et al., Neoplasia 9:200-206 (2007). In contrast, the androgen-sensitive VCaP cell line has been shown to respond to androgen stimulation with increased ERG expression (Mertz, et al., Neoplasia 9:200-206 (2007); Tomlins, et al., Science 310:644-648 (2005)). VCaP expresses AR and low levels of ERβ, but is negative for ERα.

We hypothesized that the observed connections between estrogen signaling and the TMPRSS2-ERG signature might be explained by estrogen regulation of the fusion transcript. In order to test this hypothesis, we analyzed the effect of 17β-estradiol (E2) on growth of the NCI-H660 prostate cancer cell line. NCI-H660 growth was significantly inhibited by E2, suggesting a growth inhibitory effect mediated either by ERα or ERβ. Treatment with an ERα selective agonist (propylpyrazole triol, PPT), however, resulted in growth stimulation, and treatment with an ERβ selective agonist (diarylpropionitrile, DPN) suppressed growth. Confirming the Connectivity Map and Molecular Concept Map results, we further found that the ERα agonist increased TMPRSS2-ERG expression, whereas the ERβ agonist suppressed expression of the fusion. The anti-estrogen, fulvestrant and resveretrol, a phytoestrogen with known ERβ agonistic activity, reduced the expression of the fusion transcript. Consistent with these findings, knock-down of ERβ expression by RNA interference increased TMPRSS2-ERG expression. Taken together, these results indicate that the TMPRSS2-ERG fusion can be regulated by estrogen receptor action, and that ERβ agonism results in TMPRSS2-ERG down-regulation resulting in growth suppression. The results further explain expression of TMPRSS2-ERG in an AR-negative cell line.

We then extended these observations to a second TMPRSS2-ERG cell line, VCaP, which expresses AR, but lacks high levels of expression of ERα and ERβ. Treatment of ERβ-overexpressing VCaP cells with the ERβ agonists DPN and E2 resulted in down-regulation of the TMPRSS2-ERG fusion transcript, whereas this down-regulation was not seen in non-ERβ-overexpressing cells. These results further indicate a role of estrogen receptors in regulating TMPRSS2-ERG expression.

Next, we tested the effect of the selective estrogen receptor modulator (SERM)-like compounds raloxifene and tamoxifen on TMPRSS2-ERG expression. Raloxifene has higher affinity for ERα compared to ERβ, and caused an up-regulation of TMPRSS2-ERG in NCI-H660 cells, consistent with an ERα agonist effect. In contrast, raloxifene induced a remarkable down-regulation of the fusion transcript in ERα negative VCaP-ERβ cells. From this we conclude that although raloxifene can lead to TMPRSS2-ERG down-regulation through ERβ it makes for a poor treatment alternative in TMPRSS2-ERG prostate cancers expressing ERα.

To further confirm the regulation of TMPRSS2-ERG by ERβ, we examined 5 ER binding sites previously identified in MCF7 cells upstream of the TMPRSS2 gene (Carroll, et al., Nat. Genet. 38:1289-1297 (2006)), and the TMPRSS2 promoter. Chromatin immunoprecipitation experiments showed that ERβ localized to a previously unrecognized site in the TMPRSS2 promoter in NCI-H660 cells. This result suggests that ERβ regulation of TMPRSS2-ERG expression occurs through direct transcriptional regulation of the gene fusion.

III. Discussion

Our findings have potential clinical implications. First, the expression of the TMPRSS2-ERG fusion transcript in castration resistant prostate cancers (Bonkhoff, et al., Am. J. Pathol. 155:641-647 (1999)) suggests that the TMPRSS2 promoter may remain active through ERα stimulation. Increased expression of ERα has been found to be associated with prostate cancer progression, metastasis, and the castration resistant phenotype (Bonkhoff, et al., Prostate 48:285-291 (2001)). Therefore, any clinical use of SERMs that have ERα stimulatory potential (e.g., raloxifene) may favor the progression of TMPRSS2-ERG-dependent prostate. Our data also suggests a mechanism by which ERβ may function as tumor suppressor, through negative regulation of TMPRSS2-ERG expression Cheng, et al., *FEBS Lett.* 566:169-172 (2004)). The inhibitory effect of ERβ was suggested by the Connectivity Map result that flagged phytoestrogens (e.g., resveratrol, genistein, both known to have ERβ agonistic activity) as yielding a gene expression signature that is anti-correlated with the TMPRSS2-ERG signature. Consistent with this observation, we found that activation of ERβ by DPN significantly decreased TMPRSS2-ERG expression. Importantly, loss of ERβ has been associated with prostate cancer progression (Pasquali, et al., *J. Clin. Endocrinol. Metab.* 86:2051-2055 (2001)), and castration-resistant prostate cancers often lack ERβ (Fixemer, et al., *Prostate* 54:79-87 (2003)). Such ERβ loss would be expected to result in increased TMPRSS2-ERG expression, leading to tumor cell growth stimulation. These results suggest the use of ERβ specific agonists in the treatment of prostate cancer, and raise a cautionary note regarding the use of therapeutic agents with ERα agonist activity.

We also note that these findings may have relevance for a recently initiated phase III trial testing the ability of the ERα antagonist toremifene to reduce the incidence of clinically-significant prostate cancer in a cohort of 16,000 American men (Price, et al., *Urol.* 176:965-70 (2006, see discussion 970-1)). Our results suggest that men with clinically undetected TMPRSS2-ERG fusion prostate cancers may preferentially benefit from toremifene chemopreventive treatment as compared to TMPRSS2-ERG negative prostate cancers.

Perhaps most importantly, our results suggest a mechanism by which prostate cancers which are initially androgen-dependent, might develop androgen-independence. Specifically, the TMPRSS2-ERG oncogene is regulated by estrogen receptor, whereby ERα agonists (e.g., endogenous estrogens) stimulate oncogene expression. These experiments suggest that pharmacologic inhibition of TMPRSS2-ERG expression using drugs that antagonize ERα activity and function as ERβ agonists have promise as a new therapeutic strategy for prostate cancer.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a patient for a prostate tumor comprising:
    a) assaying cells derived from said tumor to determine whether said cells carry a TMPRSS2/ERG chromosomal rearrangement;
    b) if the assay of paragraph a) indicates that said chromosomal rearrangement is present, administering to said patient a selective estrogen receptor modulator (SERM), wherein said SERM is an antagonist of the estrogen alpha receptor in prostate cells.

2. The method of claim 1, wherein said SERM is administered to said patient orally.

3. The method of claim 2, wherein said SERM is administered to said patient at a dose of 0.2-40 mg per kg body weight per day.

4. The method of claim 2, wherein said SERM is administered to said patient at a dose of 0.2-5 mg per kg body weight per day.

5. The method of claim 1, wherein said SERM is administered to said patient by injection.

6. The method of claim 1, wherein said SERM is ormeloxifene.

7. The method of claim 6, wherein said ormeloxifene is administered to said patient orally.

8. The method of claim 7, wherein said ormeloxifene is administered to said patient at a dose of 0.2-40 mg per kg body weight per day.

9. The method of claim 7, wherein said ormeloxifene is administered to said patient at a dose of 0.2-5 mg per kg body weight per day.

10. The method of claim 6, wherein said ormeloxifene is administered to said patient by injection.

11. The method of claim 1, wherein said SERM is fulvestrant and said fulvestrant is administered to said patient orally.

12. The method of claim 1, wherein said SERM is fulvestrant and said fulvestrant is administered to said patient at a dose of 0.2-40 mg per kg body weight per day.

13. The method of claim 1, wherein said fulvestrant is administered to said patient orally at 300-600 mg of fulvestrant per day.

14. The method of claim 1, wherein the assay of prostate cells in step a) is carried out using a fluorescence in situ hybridization (FISH) assay.

15. The method of claim 1, wherein cells derived from said tumor are obtained from said patient by biopsy or during surgery for said prostate tumor and said SERM is at least preferential in its action.

16. The method of claim 15, wherein cells derived from said tumor are obtained by biopsy and said SERM is administered by injection.

17. The method of claim 15, wherein said SERM is fulvestrant.

18. A method of treating a patient for a prostate tumor comprising:
    a) assaying cells derived from said tumor to determine whether said cells carry a TMPRSS2/ERG chromosomal rearrangement;
    b) if the assay of paragraph a) indicates that said chromosomal rearrangement is present, administering to said patient fulvestrant.

19. The method of claim 18, wherein said fulvestrant is administered to said patient by injection.

20. The method of claim 19, wherein said patient is administered 10-40 mg of said fulvestrant per day im.

* * * * *